(12) United States Patent
Ardenkjaer-Larsen et al.

(10) Patent No.: US 7,102,354 B2
(45) Date of Patent: Sep. 5, 2006

(54) METHODS AND DEVICES FOR HYPERPOLARISING AND MELTING NMR SAMPLES IN A CRYOSTAT

(75) Inventors: Jan Henrik Ardenkjaer-Larsen, Malmo (SE); Oskar H. E. Axelsson, Malmo (SE); Klaes Koppel Golman, Malmo (SE); Jan Wolber, Malmo (SE); Mark Howard, Canterbury (GB)

(73) Assignee: Amersham Health AS, Oslo (NO)

( * ) Notice: Subject to any disclaimer, the term of this patent is extended or adjusted under 35 U.S.C. 154(b) by 0 days.

(21) Appl. No.: 11/062,882

(22) Filed: Feb. 22, 2005

(65) Prior Publication Data

US 2005/0225328 A1   Oct. 13, 2005

Related U.S. Application Data

(63) Continuation of application No. 10/415,917, filed as application No. PCT/EP01/12737 on Nov. 2, 2001, now abandoned.

(60) Provisional application No. 60/256,974, filed on Jan. 5, 2001.

(30) Foreign Application Priority Data

Nov. 3, 2000   (SE) ..................... 0004034

(51) Int. Cl.
*G01V 3/00* (2006.01)
*A61B 5/055* (2006.01)
*F27B 1/09* (2006.01)

(52) U.S. Cl. ............... 324/321; 324/307; 600/411; 219/385; 219/390; 219/392

(58) Field of Classification Search ........... 600/420, 600/412; 219/385; 62/637; 324/309; 264/0.5
See application file for complete search history.

(56) References Cited

U.S. PATENT DOCUMENTS

| 4,642,206 A | * | 2/1987 | Honig .................. 264/0.5 |
| 5,258,710 A | * | 11/1993 | Black et al. ............ 324/309 |
| 5,617,859 A | * | 4/1997 | Souza et al. ............ 600/420 |
| 5,626,137 A | | 5/1997 | Dumoulin et al. ........ 600/420 |
| 6,125,654 A | * | 10/2000 | Honig .................. 62/637 |
| 6,278,893 B1 | | 8/2001 | Ardenkjaer-Larson et al. ............... 600/420 |
| 6,305,190 B1 | | 10/2001 | Driehuys et al. ........ 62/637 |
| 6,466,814 B1 | | 10/2002 | Ardenkjaer-Larsen et al. ............... 600/420 |
| 6,515,260 B1 | * | 2/2003 | Anderson .............. 219/385 |
| 6,666,047 B1 | | 12/2003 | Shah et al. ............ 62/637 |
| 2004/0049108 A1 | * | 3/2004 | Ardenkjaer-Larsen et al. ............... 600/412 |
| 2005/0225328 A1 | * | 10/2005 | Ardenkjaer-Larsen et al. ............... 324/321 |

FOREIGN PATENT DOCUMENTS

| WO | WO95/06882 | * | 3/1995 |
| WO | WO99/35508 | * | 7/1999 |
| WO | 0023797 | | 4/2000 |
| WO | WO00/72031 | * | 11/2000 |
| WO | WO02/36005 A1 | * | 5/2002 |

* cited by examiner

*Primary Examiner*—Diego Gutierrez
*Assistant Examiner*—Tiffany A. Fetzner
(74) *Attorney, Agent, or Firm*—Robert F. Chisholm

(57) ABSTRACT

The present invention relates to devices and method for melting solid polarised sample while retaining a high level of polarisation. In an embodiment of the present invention a sample is polarised in a sample-retaining cup 9 in a strong magnetic field in a polarising means 3a, 3b, 3c in a cryostat 2 and then melted inside the cryostat 2 by melting means such as a laser 8 connected by an optical fibre 4 to the interior of the cryostat.

9 Claims, 3 Drawing Sheets

METHODS AND DEVICES FOR HYPERPOLARISING AND MELTING NMR SAMPLES IN A CRYOSTAT

This application is a continuation of application Ser. No. 10/415,917 filed Aug. 29, 2003 now abandoned which is a filing under 35 U.S.C. § 371 and claims priority to international application number PCT/EP01/12737 filed Nov. 2, 2001 which claims priority to U.S. Provisional application No. 60/256,974 filed Jan. 5, 2001 and to Norwegian application 20012256 filed May 8, 2001 and to Swedish application 0004034-5 filed Nov. 3, 2000 the entire disclosure of which is hereby incorporated by reference.

FIELD OF THE INVENTION

The present invention relates to devices and methods for melting solid polarised samples while retaining a high level of polarisation.

PRIOR ART

The present invention relates to nuclear magnetic resonance (NMR) analysis, particularly to nuclear magnetic resonance imaging (MRI) and analytical high-resolution NMR spectroscopy. MRI is a diagnostic technique that has become particularly attractive to physicians as it is non-invasive and does not involve exposing the patient under study to potentially harmful radiation such as X-rays. Analytical high resolution NMR spectroscopy is routinely used in the determination of molecular structure.

MRI and NMR spectroscopy lack sensitivity due to the normally very low polarisation of the nuclear spins of the samples used. A number of techniques exist to improve the polarisation of nuclear spins in the solid phase. These techniques are known as hyperpolarisation techniques and lead to an increase in sensitivity. However, in order to exploit the NMR signal for in vivo medical imaging the polarised sample has to be brought into solution before being introduced into the imaging object. In addition, for in vitro analytical NMR spectroscopy, it can also often be advantageous to bring the polarised solid sample into solution. A problem exists in that the polarised solid sample has to be brought into solution and transferred into the NMR magnet with a minimal loss of polarisation. Patent application no. WO9935508 mentions a method for dissolving solid polarised sample. In this method the polarised sample was manually lifted out of the cryostat and within about 1 second dissolved in deuterium oxide at 40° C. while being subjected to a magnetic field of 0.4 T. This method enhanced the polarisation by a factor of up to 21 compared to other methods of producing a solution containing polarised sample. However this method has the disadvantage that as the sample is moved manually it is difficult to get reproducible results. This is because the polarisation is affected by the speed and smoothness of the lifting of the polarised sample out of the cryostat and it is very difficult for different operators to ensure that they lift the polarised sample at the same speed and in a fluid movement. The purpose of the present invention is to provide methods and devices for improving the prior art method for producing a polarised sample with a high level of polarisation.

SUMMARY OF THE INVENTION

According to the present invention, at least some of the problems with the prior art are solved by means of a device having the features present in the characterising part of independent claim 1, and methods having the features mentioned in the characterising part of claim 6. In particular the present invention provides a method and means for melting a polarised solid sample from a polarising unit with a minimal loss of polarisation. Devices and methods for producing melted (hyper)polarised samples, e.g. contrast agents or analytical samples, are described.

Further improved devices and methods have the features mentioned in the dependent claims.

In one method and device in accordance with the present invention a polarising apparatus is provided with means for melting a sample polarised by the polarising apparatus, e.g. the solid polarised sample is melted while inside the device in which it was polarised. In a preferred embodiment of the invention, the polarising chamber of the polarising unit and the melting chamber are combined in a single chamber. In an especially preferred embodiment of the invention, the polarising and melting chamber is combined with a NMR spectrometer and/or NMR imager so that the melted polarised sample may be analysed in the same device that it was melted in. In accordance with the present invention, polarisation may be achieved by, amongst others, the use of a polarising agent, e.g. a compound comprising paramagnetic organic free radicals. The NMR data obtained by the use of devices and methods in accordance with the present invention may be NMR imaging data and/or NMR spectroscopy data.

DETAILED DESCRIPTION OF EMBODIMENTS ILLUSTRATING THE INVENTION

Figure 1:
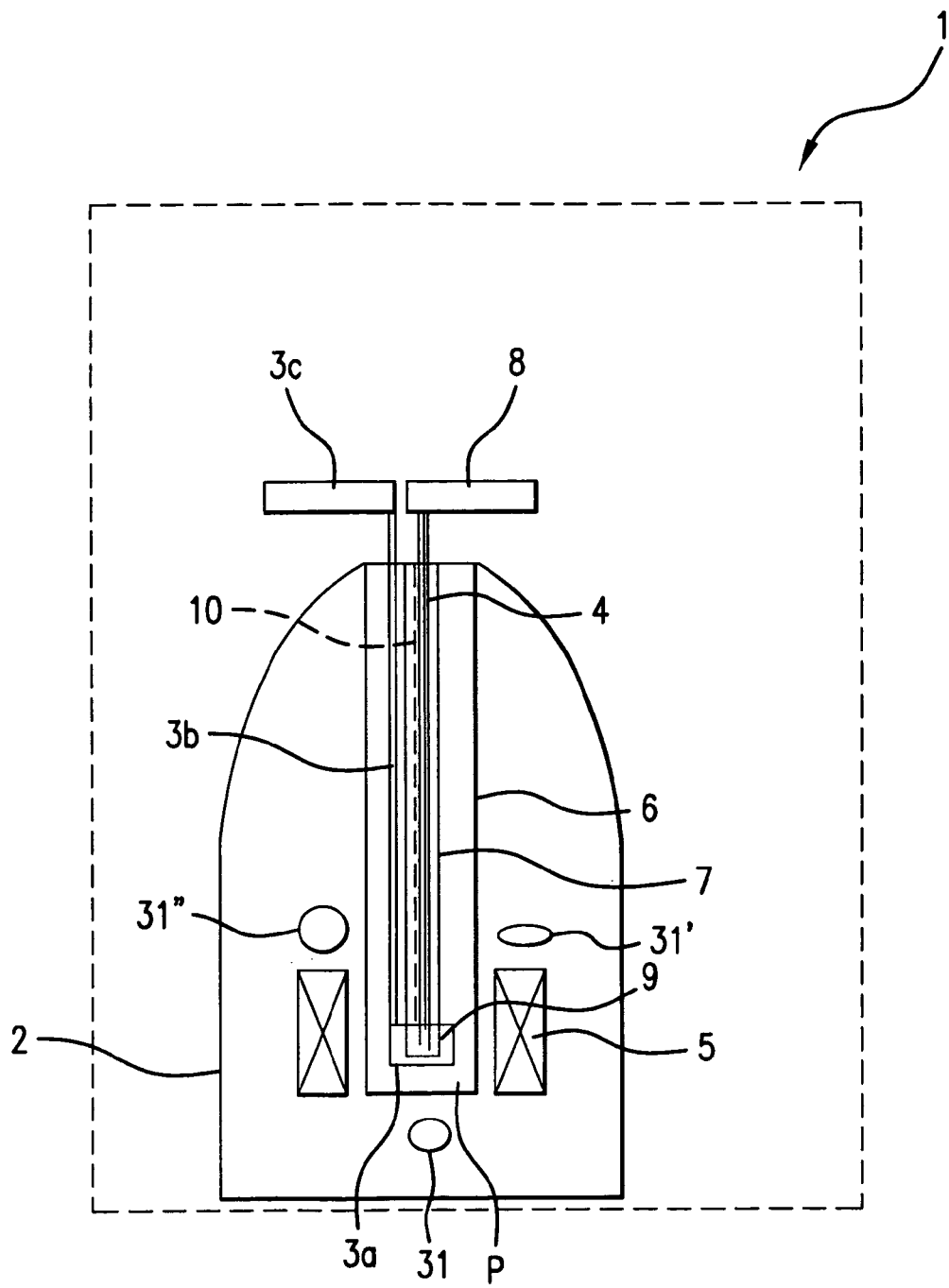
FIG. 1 shows a schematic lateral view of a first embodiment of a device in accordance with the present invention.

In methods and devices in accordance with the present invention, a solid sample of the sample to be polarised can be polarised while still in the solid phase by any appropriate known method, e.g. brute force polarisation, dynamic nuclear polarisation or the spin refrigerator method, while being maintained at a low temperature (e.g. under 100 K) in a strong magnetic field (e.g. 1–25 T). After the solid sample has been polarised, it is melted with a minimum loss of polarisation. In the following the expression "melting means" will be considered to mean the following: a device capable of providing sufficient energy to the solid polarised sample to melt it.

In an embodiment of the present invention the melting takes place in a combined polarisation, melting and NMR analysis device.

The advantage of the described invention is that it provides means for bringing polarised solid sample into solution with minimal loss of polarisation in a repeatable manner. This is crucial to the use of the solid state hyperpolarisation techniques in medical imaging and analytical in vitro high-resolution NMR spectroscopy. In solution, the NMR lines are narrow. This improves considerably the signal-to-noise ratio and spectral resolution, and also gives technical advantages since the sample does not have to be spun as for solid samples.

For most solid samples, the relaxation rate (loss of polarisation if hyperpolarised) increases rapidly as a function of inverse field strength. Therefore, for these polarised samples it is preferable that they are kept in a strong magnetic field (e.g. greater than 0.1 T) while being handled. Other reasons for the loss of polarisation are also known, e.g. sudden changes of magnetic field orientation, strong magnetic gradients, or radio frequency fields, and these should be avoided as much as possible. The melting of the polarised sample can be promoted by several methods, e.g. ultra sound, microwave heating, laser irradiation, radiation or conduction or any other means that will deposit into the solid sample the energy required to melt it. The relaxation rate as a function of temperature and field is unique to every solid sample and solvent/solute system. It is therefore advantageous to optimise the temperature of the process for minimal relaxation of the actual sample being melted. In general, but not always, the magnetic field should be as strong as possible. The minimum $T_1$ during the process will generally increase with increasing magnetic field.

In a preferred embodiment of the present invention, a device for melting a solid polarised sample is provided in a dynamic nuclear polarisation (DNP) system. This DNP system comprises a magnet with field strength of 0.1–25 T or more that is placed in a low loss cryostat in order to achieve optimal cryogenic hold times. For magnetic fields above ca. 2 T the magnet may be superconducting. For lower fields simpler magnets could be preferred. An especially preferred DNP system consists of a superconducting magnet designed for a field-strength of 2–25 T. The magnet is placed in an ultra low loss cryostat to achieve optimal cryogenic hold time. The field homogeneity required is sample dependent, but will typically have to be +/−0.2 mT over the sample volume. This can be achieved by providing field shims even for large samples. Correspondingly, the stability of the field during polarisation should be better than the homogeneity criterion, i.e. the field drift should be less than the inhomogeneity. The magnet is designed to accommodate a low temperature space to cool the sample. The preferred superconducting magnet cryostat is preferably provided with a pumped helium bath or at least a cold space in the bore of the magnet. The helium bath may be contained in a tube that is thermally insulated (e.g. vacuum insulated) from the magnet helium reservoir but connected to it by a capillary to allow filling from the magnet reservoir. The low temperature space may simply be a cylinder (made from thin-walled stainless steel or copper or another non-magnetic material or combinations thereof) with the lower end closed. In order to obtain the lowest possible temperatures and lowest cryogenic consumption, the low temperature space is preferably placed in vacuum inside the helium can of the superconducting magnet and the low temperature cylinder can preferably be thermally anchored at appropriate places in the bore, for example to the helium vapour-cooled shield and the liquid nitrogen-cooled shield or the like. The low temperature cylinder can preferably be connected to the helium can through a capillary at its base. The flow of helium may be controlled by a needle valve regulated from exterior, manually or automatically by computer control means or the like. The flow of helium into the helium bath may be controlled by a motorised needle valve. The level of the liquid can be monitored, e.g. by an Allen Bradley carbon resistor meter, and the needle valve controlled manually or automatically to maintain a fixed level. In order to achieve lower temperatures of the order of 1 K ($^4$He), the bath can be pumped and the temperature of the bath can be ascertained through the helium vapour pressure measured, for example, by an absolute capacitance transducer or Pirani element. If cooled by gas then a temperature measurement can be used to control the needle valve. The cryogen, e.g. helium or nitrogen, could also be supplied from an external reservoir. Closed cycle refrigerators ('cryogen free') could also be envisaged, both for magnet cooling and cooling of the cold space. The sample is polarised by microwave irradiation at the proper frequency. A microwave arrangement is provided for irradiation. The microwave arrangement can be implemented in a number of ways. For lower frequencies (less than ca. 200 GHz) a wave-guide may be used to guide the waves to the sample space. At higher frequencies quasi-optical methods can be employed. The sample space is preferably constructed as a resonant microwave structure. The microwave structure is preferably configured to allow easy placement and exchange of samples and an efficient cooling of samples. Once polarised the sample is melted by means of a device and method in accordance with the present invention as described below.

An embodiment of the present invention is illustrated schematically in FIG. 1. FIG. 1 shows an example of a cryostat device 1 for polarising a solid sample which device 1 is provided with solid polarised sample melting means in accordance with the present invention. Device 1 (shown enclosed by dashed lines) comprises a cryostat 2, containing a polarising means 3, e.g. a microwave chamber 3a connected by a wave guide 3b to a microwave source 3c, in a central bore 6 surrounded by magnetic field producing means such as superconducting magnet 5. Cryostats and polarising means for polarising solid sample are well known from the prior art and their constructions will not be described in detail. The bore 6 extends vertically down to at least the level of a region P near the superconducting magnet 5 where the magnetic field strength is sufficiently high, e.g. between 1–25 T or more, for example 3.5 T, for polarisation of the sample to take place. The central bore 6 is sealable and can be evacuated to low pressures e.g. pressures of the order of 1 mbar or less. A sample-introducing means such as a removable sample-transporting tube 7 can be contained inside the bore 6 and this tube 7 can be inserted from the top of the bore down to a position inside the microwave chamber 3a in region P. Region P is cooled by liquid helium to a temperature low enough for polarisation to take place, e.g. temperatures of the order of 0.1–10 K. Tube 7 can be sealed at its upper end in any suitable way in order to retain the partial vacuum in the bore 6. A sample-retaining container, such as a sample-retaining cup 9, can be, preferably removably, fitted over the lower end of sample-transporting tube 7. This cup 9 covers the bottom of tube 7 and is intended to hold any sample introduced into tube 7. Cup 9 is preferably made of a light-weight material with a low specific heat capacity such as a foamed plastic, e.g. polystyrene, so that the heat capacity of the cup 9 is as low as possible. A sealable He inlet tube 10 (shown by a dashed line for ease of illustration) extends from the top of bore 6 to the base of cup 9.

In a method in accordance with the present invention, a sample in the sample-retaining cup 9 is polarised in the normal manner and then brought into a liquid phase by being melted. This melting of the polarised sample in the sample-retaining cup 9 is performed while the polarised sample is still inside the cryostat device 1. This can be achieved by providing a means for applying energy to the polarised solid sample, e.g. ultra sound, electromagnetic energy, or by bringing the solid polarised sample into contact with a warm surface or substance. In the device shown in FIG. 1 the solid polarised sample is melted in the sample-retaining cup 9 by a means for applying energy to the polarised solid sample in the form of a laser 8 mounted outside the cryostat which fires electromagnetic radiation though an optical fibre 4 onto the sample in the sample-retaining cup 9.

An example of a embodiment of a method in accordance with the present invention for melting a solid sample that has been polarised while in the solid state has the following steps:

The sample, preferably in the form of powder, grains or beads in order to facilitate rapid and even melting, but possibly in the form of a liquid at room temperature, is introduced into the sample-retaining cup 9 at bottom of the sample-transporting tube 7;

sample-transporting tube 7 is introduced into bore 6 so that sample-retaining cup 9 is positioned in a magnetic field of the necessary field strength, bore 6 is made vacuum tight and evacuated to its working pressure;

the still solid sample is polarised, preferably hyperpolarised;

bore 6 is pressurised to atmospheric pressure;

if the sample-retaining cup 9 is under the surface of the liquid helium in the cryostat then the sample-transporting tube 7 is raised until it is above the surface of the helium;

the means for applying energy to the polarised solid sample is activated, energy is applied to the solid sample, e.g. by laser 9 and optical fibre 4, and the solid sample melted.

Optionally, a further step of analysing the polarised liquid sample by NMR is performed.

Preferably this method is automated, for example by being controlled by computer (not shown).

When the polarised solid sample is melted inside the polarising unit then the polarised solid sample is preferably melted while kept in the strong magnetic field of the polarising unit or close to the strong magnetic field area of the magnet in order to minimise any loss of polarisation of the sample. If the sample is polarised in a helium (or nitrogen) bath, the sample can be raised from the bath a short distance e.g. 5 cm or 10 cm to drain the liquid coolant prior to melting. The sample would still experience a significant part of the magnetic field of the polarising unit. The solid sample could then be melted and, optionally, analysed by NMR.

In the embodiment of the present invention shown in FIG. 1, the analytical NMR instrument is provided in the same instrument as the polarising unit and melting unit. This is shown in FIG. 1 by a plurality of analysis coils 31–31", i.e. nuclear magnetic resonance imaging coils and/or nuclear magnetic resonance spectroscopy coils. Coils which can be used for field shimming and NMR signal acquisition can be placed in positions that are known from high resolution analytical NMR. In this case, the melting of the polarised sample takes place in the same area as the imaging of the melted polarised sample and the transport time between the melting area and the imaging area is zero. This is advantageous, as in this case there is no need to move the sample out of the magnetic field of the superconducting magnet when performing the analysis i.e. imaging or spectroscopy, and the loss of polarisation of the sample due to transporting is eliminated. The loss of polarisation between the polarisation in the solid state and the polarisation in the melted state can be minimised by rapidly melting the sample. Additionally, the low operating temperature of the coils immersed in liquid helium improves their signal to noise ratio by a significant factor (of more than 3).

However, in some cases, the requirements concerning field strength and temperature may not be identical for the polarisation and the NMR detection, and means may be provided for moving a sample from one part of the magnet to another. The NMR detection could advantageously be done at a lower or higher field than optimal for the DNP process. One implementation would therefore be that the DNP polarisation is performed in cold helium gas at the lower edge of the magnet (i.e. in a lower field, e.g. 3.35 T). The field would then have to be shimmed in this area to the required homogeneity. After being polarised the sample could be lifted to the magnet centre (that has a higher field, e.g. 9.4 T, and homogeneity) for melting and NMR detection. Furthermore, the sample could be lifted to an intermediate place for melting and then moved to the magnet centre for NMR detection.

A conceivable variation of the invention is the incorporation of a multiple sample holder into the device so that several samples can be polarised at once or sequentially and melted one by one. It is also conceivable to use a system where several samples are melted and analysed simultaneously. As is obvious to the skilled person, a multiple sample holder system can be fashioned in many different ways e.g. using a carousel type holder or a grid-type holder.

In one embodiment it is possible to provide prior art NMR equipment with a device in accordance with the present invention in order to produce an apparatus that can produce samples with a high polarisation by DNP. In order to do this the NMR equipment needs to be provided with a low temperature space that is in a magnetic field. In order to achieve this, any ordinary NMR magnet that has a suitably wide bore size may be equipped with a flow cryostat and instrumentation as described below in order to enable the production of solutions of molecules with DNP enhanced nuclear polarisation. A flow cryostat is a vacuum insulated chamber that may be inserted into the bore of a magnet normally designed to have a room temperature bore, thereby allowing the temperature of the bore to be lowered by a stream of a cold cryogen. The flow cryostat is usually connected to an external cryogen supply through a transfer line and the flow of cryogen into the flow cryostat cools the bore of the magnet and forms a low temperature space. The flow cryostat may be equipped with means, described below, to enable the polarisation of solid samples by DNP and it may be equipped with instrumentation, described below, for the detection of nuclear signals in the solid state and in solution. Note that in dedicated DNP systems for NMR analysis or production of hyperpolarised imaging agents the low temperature space is preferably integrated into the magnet cryostat.

Melting by laser can be chosen as an example of the method. A diode laser, or any other known laser or light-source, with an output power of 100 W is a common commercial product. This would take a water-based sample of 1 µl (ca. 1 mg) from 1 K to 300 K in 6.4 ms.

Cp(ice)=1.67 J/K/g (not constant with temperature, intentionally overestimated)
Cp(water)=4.18 J/K/g
Heat of fusion=79.8 J/g
m(water)=1 mg
Energy(1–273K)=1.67 J/K/g*272K*1 mg=450 mJ
Energy(melt)=79.8 J/g*1 mg=80 mJ
Energy(273–300K)=4.18 J/K/g*27K*1 mg=113 mJ
Total=643 mJ
Time to deliver 643 mJ by a 100 W laser=643 mJ/100 W=6.4 ms Using a less powerful laser would increase the melting time proportionally. Diode lasers are available at a number of wavelengths at these power levels and the solid sample itself would preferably be able to absorb the light energy, or it could be doped with an absorbing molecule, or the interface to the solid sample could be coated with an absorbing material. Thus the wavelength can be chosen to match the absorption characteristics of the solid sample or the plate that it is supported on. A sample plate material with good absorption of the laser energy and low thermal conductivity is preferable for good melting efficiency. A current controlled mirror can control the laser beam or, alternatively, the sample may be moved and the laser kept stationary.

In an another embodiment of the present invention the polarised solid sample is melted by bringing it into thermal contact with a warm liquid. This can be achieved by injecting or inserting the sample as a liquid (which would subsequently be frozen e.g. in the cryostat) or flowable solid e.g. powder, beads, etc. into a sample-receiving space in a capillary. Optionally the sample receiving-space may be surrounded by a solenoid coil. The capillary can be introduced into the cryostat and the sample frozen and polarised as described above. After the polarisation a volume of hot liquid may be injected into the sample receiving-space through the capillary tube and the solid sample rapidly melted. Alternatively the sample receiving space could be surrounded by, and in thermal contact with, a means for applying energy to the polarised solid sample in the form of a chamber or coil of tubing able to be filled with a hot liquid. In this way the polarised sample can be melted by heat energy transferred from the hot liquid into the sample-receiving space though the walls of the chamber or coil. In this way, dilution of the sample is avoided. Preferably the injected liquid will also serve as a susceptibility matching medium for the solenoid coil. The melted polarised sample can be analysed in situ or alternatively flushed out of the capillary to a separate spectroscopy or imaging area.

While heating with a laser and hot liquid have been described, any method of applying energy may be used and indeed a combination of sources for applying thermal energy to the sample is possible. For example the laser melting could be assisted by an electrical heat element. It is important that the melting happens on a time scale of T1 (or preferably less) for the nuclear spin. The loss of polarisation during the melting should be less than 99%, preferably less than 90% and even more preferably less than 10% and these different levels of loss of polarisation can be reproducibly achieved by adapting the speed of melting of the polarised solid sample. It is also preferable that the supply of energy to the sample is regulated to maintain the sample liquid after melting so that imaging can be performed on the melted sample.

Figure 2:
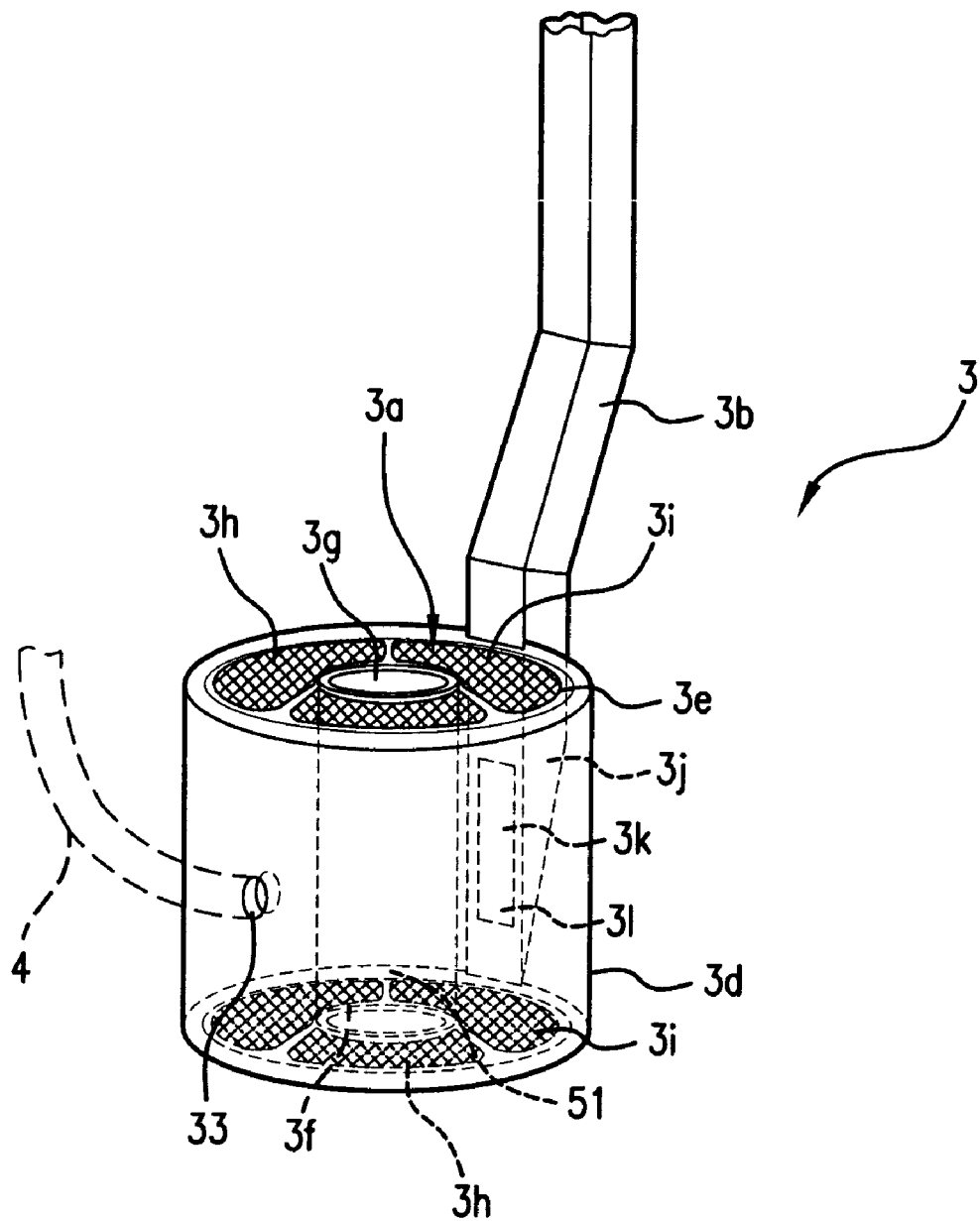
FIG. 2 shows an embodiment of a sample-retaining container in accordance with the present invention.

A sample holder and a suitable microwave structure may be placed in the cold space in order to achieve microwave irradiation of the sample. The microwave structure can be a horn antenna or a chamber attached to the end of a wave-guide (as shown in FIG. 2) or a set of Fabry-Perot mirrors or any other suitable microwave irradiating structures. The microwave structure is preferably designed to act as a resonance chamber for microwaves in order to increase the strength of the microwave field in the microwave structure. For the lower frequencies (less than ca. 200 GHz) wave-guides may conveniently be used to guide the waves to the irradiating structure. The geometry and dimensions of the wave-guide are chosen in order to reduce microwave losses. Preferably the wave-guide is designed to have as low a heat load to the low temperature space as possible, and can be made, for example, from silver plated thin-walled stainless steel. Corrugated wave-guides could also be used. At higher frequencies quasi-optical methods can be employed, and the microwave can be guided with lenses and mirrors. The microwave structure preferably has openings to allow an easy exchange of sample and efficient cooling of the sample. A suitable microwave oscillator generates the microwaves, e.g. an IMPATT diode oscillator, or an IMPATT amplified Gunn oscillator, or a BWO or the like. Furthermore, the microwave oscillator may be an integrated part of the resonant structure for irradiating the sample. Thus the active device producing the microwaves may be physically placed in the magnet close to the sample whereby transmission losses would be reduced.

FIG. 2 shows a perspective view of part of an embodiment of a polarising means 3 intended to be placed inside the cryostat of a DNP system. This comprises a microwave chamber 3a connected by a wave-guide 3b to a source of microwave energy (not shown). Chamber 3a has a substantially cylindrical outer wall 3d, an upper end plate 3e and a lower end plate 3f. Chamber 3a is made of a microwave reflecting material such as brass. Upper end plate 3e has a central circular opening 3g with a diameter adapted to allow a sample-retaining cup 9 (not shown) to pass into the chamber 3a. Upper and lower end plates 3e, 3f have a plurality of cut-outs 3h which are covered by a microwave reflecting mesh 3i which allows liquid helium to enter the chamber 3a while preventing microwaves from leaving the chamber 3a through the cut-outs 3h. The chamber 3a is mounted on the lower end 3j of the wave-guide 3b and a slot 3k in the wall 3d of the chamber 3a is aligned with a similar slot 31 in the lower end 3j of the wave-guide 3b in order to allow microwaves to pass from the wave guide 3b into the chamber 3a. The dimensions of the slots 3k, 31 are adapted to optimise the flow of microwaves into the chamber 3a. For example, if the inner diameter of the chamber is 28 mm, the inner height is 28 mm and the internal width of the wave-guide is 7 mm, then the slots can be 5–10 mm high and 2–7 mm wide. The lower end 3j of the wave-guide 3b is tapered towards the bottom in order to act as a microwave reflector for increasing the amount of microwave energy coupled into the chamber 3a. Suitable angles of taper depend on the dimensions of the wave-guide, the microwave frequency used and the dimensions of the slots 31, 31, but can be from about 5° to 60°, but preferably from 15° to 30°. The dimensions of the chamber 3a, wave-guide 3b, slots 3k, 31 are adapted so that chamber 3a acts as a resonance chamber for the microwave energy. In order to measure the polarisation of a sample contained in a sample-retaining cup, the chamber can be optionally provided with a central NMR pick-up coil 51. This can be suitably made of a cylinder made of PTFE provided with, depending on the static field orientation, helical or saddle shaped copper windings (not shown) and connected to suitable sensing means.

In this embodiment, a sample is placed in a sample-retaining cup 9 lowered into the centre of the chamber 3a (inside the pickup coil if there is a pick up coil). The source of microwave radiation is activated and the sample irradiated until it is polarised. It can then be melted by means of the means for applying energy to the polarised sample, e.g. a optical fibre 4 (shown by a dashed line for ease of illustration) attached to a laser 8, described above and shown in FIG. 1, and connected to a laser light inlet port 33 on the wall 3d so that the laser light transmitted though the optical fibre 4 is directed onto the polarised solid sample.

In a second embodiment of a chamber in accordance with the present invention, the lower end plate 3f has a central hole 3m of the same diameter as a sample-retaining cup 9. This allows the sample-retaining cup 9 to be lowered through the chamber 3a and out the bottom of it. A sample-receiving container could be provided with a plurality of vertically separated sample-retaining cups. These cups could each be the height of the chamber 3a or a fraction thereof. If they are the same height as the chamber 3a then it would be possible to expose a first sample in one cup to microwaves in the chamber 3a while a second sample in a second cup is positioned outside the chamber, but still very close to the strong magnetic field. When the first sample is sufficiently polarised the sample receiving container can be moved vertically so that the second sample in the second cup is inside the chamber 3a and the polarised first sample in the first cup is maintained polarised in the magnetic field outside the chamber 3a. This can be repeated until all the samples have been polarised, then all the samples can be melted at once, using one means, or a plurality of means, for applying energy to the polarised solid sample. Alternatively, each polarised sample could be melted in turn in the strong magnetic field in the DNP unit or in the magnetic field of an imaging or spectrometry device.

NMR detection is particular desirable for analytical applications. For other applications NMR detection optionally provides a measure of the nuclear polarisation. The NMR detection coil could be of any known design, e.g. solenoid or saddle shaped. Usually the coil (inductance) is tuned to the NMR frequency with a capacitor and matched to the characteristic impedance of the cabling. The NMR coil could be tuned and matched at a number of frequencies in order to detect the nuclei of interest of more than one nuclear species. The capacitors could be mounted close to the coil in the cold space. This would allow the highest Q-values to be obtained. In the event that it is impractical to have the capacitors close to the coil, then they may be put outside the cold space and connected to the low temperature space via a transmission line. The transmission line could be coaxial, twisted pair, stripline, or any other suitable cabling. The choice will be a compromise between heat load to the cold space and signal attenuation. Several coils could also be envisaged. They could be tuned for two NMR frequencies and would allow double resonance NMR (decoupling, cross polarisation, etc) to be performed in both solid state and liquid phase. This would also allow simultaneous detection of more nuclei. The spectrometer would then have to have multiple receivers. Optionally, the NMR signal of the various nuclei could be acquired sequentially. In order to permit multiple samples to be analysed in a short space of time, a sample-carrousal for moving samples may be provided. Additionally, the melting of the solid sample may be detected by optical means, as in order to perform reproducible NMR analysis. This may be checked by using optional optical photo-detection means inside or outside the NMR analytical chamber. Since some of the nuclei of interest may have very short $T_1$ values it can be important to secure analysis as soon as the melting process is finished. It is therefore preferable to have means arranged for coincident excitation/detection of all nuclei of interest. If the NMR detection circuit is cooled then a better signal-to-noise ratio is obtained. Furthermore, cooling of the signal amplifier is often advantageous. Consequently the signal amplifier may be positioned close to the NMR detection circuit and preferably in the cold space. Superconducting coils and SQUID detectors are other devices that are available to improve the signal-to-noise ratio.

Figure 3:
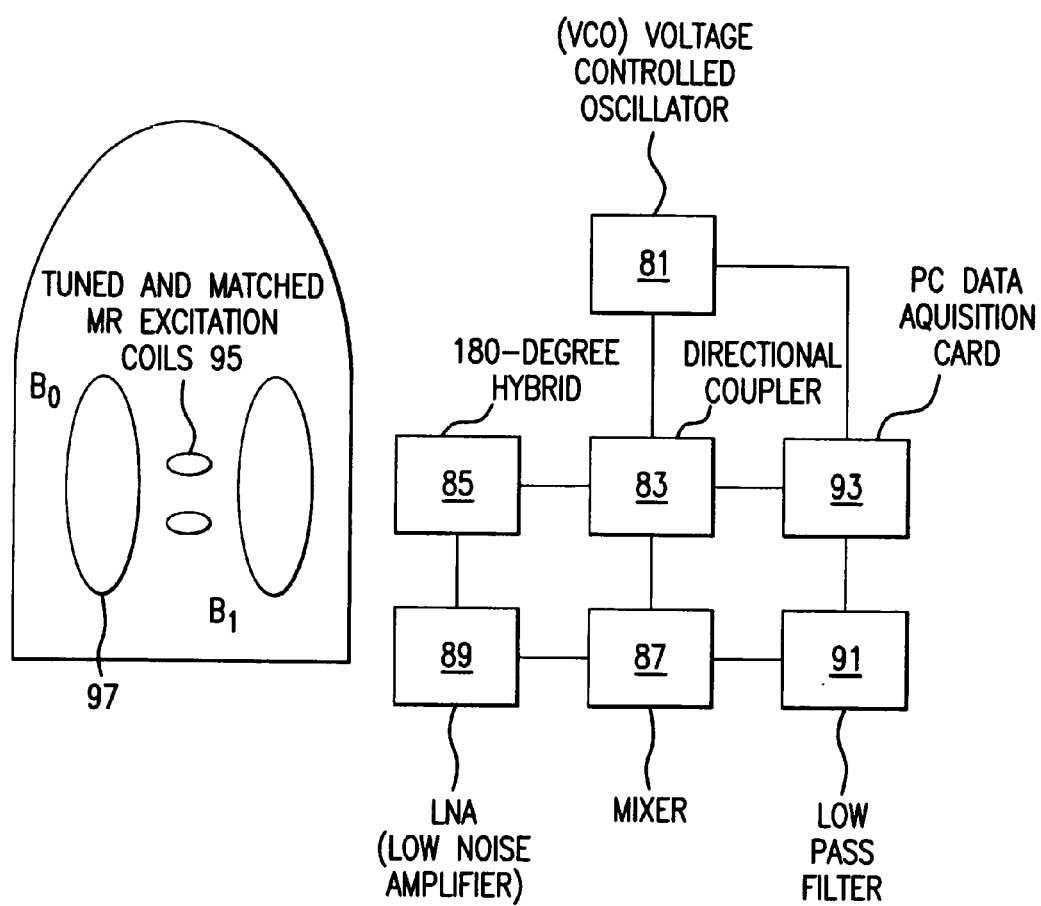
FIG. 3 shows schematically an embodiment of a magnetic resonance measurement circuit.

A simple and cheap circuitry that can be used for simple polarisation measurements is shown in FIG. 3. The device is a simple radio frequency magnetic resonance spectrometer. Such a device can be used to determine the polarisation of the solid sample before it is melted and uses any of the previous described detection coils. The RF circuit consists of a VCO (voltage controlled oscillator) 81, a directional coupler 83, a 180-degree hybrid 85, a mixer 87, a LNA (low noise amplifier) 89, a low pass filter 91, a PC data acquisition card 93, and tuned and matched MR (or excitation) coils 95 (giving magnetic field $B_1$) arranged to provide a nearly uniform field transverse to the direction of the static field $B_0$ from static field coils 97. The coils 95 are tuned to the MR frequency and matched to the characteristic impedance of the transmission line (e.g. 50 Ω). The VCO 81 (or function generator) generates a continuous wave signal that is split by directional coupler 83 (divider) into two signals, which drives the local oscillator of the mixer 87 and the other to 180-degree hybrid 85 feeding the MR coil 95. Fixed attenuators (not shown) may be used to adjust the signal levels. The VCO 81 should be capable of being frequency modulated over a sufficient frequency range to cover the spectra range of interest. The modulation rate could be typically 5–50 Hz, and the modulation signal is supplied synchronously with the signal acquisition (signal averaging). Preferably the modulation-signal and signal acquisition is generated from a PC data acquisition card 93, and the signal is conveniently available for further data analysis. A change of reflection coefficient is observed as the frequency is swept through the magnetic resonance. The reflection signal is amplified by the LNA 89 and fed to the mixer 87. By adjusting cable lengths an absorption or dispersion signal can be chosen. The bandwidth of the MR coils 95 in itself produces a parabolic baseline, which has to be subtracted from the signal. The baseline can be acquired before introducing the sample or it can be fitted with a polynomial function (or a spline function) outside the signal regions. The coil bandwidth can be adjusted for optimal performance in a number of ways, e.g. resistive damping, overcoupling which gives a better result, or, preferably, by actively loading the coils 95 with the LNA 89. The natural bandwidth of a tuned coil in this frequency regime is several hundred Hz, providing insufficient bandwidth for most applications. Resistive damping increases the useful bandwidth to an acceptable degree. However, this compromises the signal-to-noise ratio by the square root of the increase. This is acceptable to some extent since amplitude and phase-noise of the VCO often determine the signal-to-noise ratio. The magnetic field could be anything from a few mT to many T depending on the gyromagnetic ratio of the spin and the frequency of the VCO 81.

The above mentioned embodiments are intended to illustrate the present invention and are not intended to limit the scope of protection claimed by the following claims.

The invention claimed is:

1. A device configured for melting a solid hyperpolarised sample, comprising:
    a cryostat;
    coils within said cryostat;
    a means for hyperpolarising said solid sample at a low temperature within the cryostat, wherein the means for hyperpolarizing is also located within a magnetic field generated within the device
    a means for melting said hyperpolarised solid sample wherein said means for melting is positioned inside said cryostat and within said generated magnetic field; and
    wherein said coils within said cryostat are configured for performing an NMR analysis of a melted hyperpolarised sample.

2. A device in accordance with claim 1, wherein said means for melting said hyperpolarised solid sample are configured to melt said sample rapidly such that the loss of polarisation of said hyperpolarised sample during melting is less than 99%.

3. A device in accordance with claim 1, wherein said means for melting said hyperpolarised solid sample is configured to melt said sample rapidly such that the loss of polarisation of said hyperpolarised sample during melting is less than 90%.

4. A device in accordance with claim 1, wherein said means for melting said hyperpolarised solid sample is configured to melt said sample rapidly such that the loss of polarisation of said hyperpolarised sample during melting is less than 10%.

5. A device in accordance with claim 1, wherein said means for melting said hyperpolarised solid sample and said coils are configured such that melting of said hyperpolarised sample may take place in the same area as analysing of said melted hyperpolarised sample.

6. A method for producing a melted hyperpolarised sample comprising the steps of:
   introducing a solid or liquid sample into a device containing a cryostat wherein said cryostat comprises means for hyperpolarising a sample at low temperature inside a magnetic field generated in said device;
   freezing said sample;
   hyperpolarising said frozen sample inside said cryostat;
   melting said hyperpolarised frozen sample while still inside said cryostat and inside said magnetic field; and,
   performing NMR analysis of said melted hyperpolarised sample while the melted sample is within said cryostat and inside said magnetic field.

7. A method in accordance with claim 6, wherein said step of melting said hyperpolarised sample is performed rapidly such that the loss of polarisation of said hyperpolarised sample during said melting step is less than 99%.

8. A method in accordance with claim 6, wherein said step of melting said hyperpolarised sample is performed rapidly such that the loss of polarisation of said hyperpolarised sample during said melting step is less than 90%.

9. A method in accordance with claim 6, wherein said step of melting said hyperpolarised sample is performed rapidly such that the loss of polarisation of said hyperpolarised sample during said melting step is less than 10%.

* * * * *